United States Patent [19]

Watson

[11] Patent Number: 4,657,138

[45] Date of Patent: Apr. 14, 1987

[54] CARRYING CASE FOR INSULIN SYRINGES

[76] Inventor: Frank K. Watson, 3116 Beechwood Ave., Flint, Mich. 48506

[21] Appl. No.: 850,611

[22] Filed: Apr. 11, 1986

[51] Int. Cl.⁴ .......................... B65D 5/50; B65D 85/24; B65D 69/00

[52] U.S. Cl. ..................................... 206/366; 206/571; 206/523; 206/564; 206/587; 206/590; 206/592

[58] Field of Search ............... 206/366, 521, 523, 562, 206/563, 564, 571, 587, 588, 589, 590, 591, 592, 45.34, 483

[56] References Cited

U.S. PATENT DOCUMENTS

| | | | |
|---|---|---|---|
| 2,228,493 | 1/1941 | Will | 206/214 |
| 3,367,483 | 2/1968 | Studen | 206/45.34 |
| 3,768,635 | 10/1973 | Eggert | 206/366 |
| 4,243,140 | 1/1981 | Thrun | 206/523 |
| 4,429,793 | 2/1984 | Ehmann | 206/571 |
| 4,446,970 | 5/1984 | Fürther | 206/571 |
| 4,524,868 | 1/1985 | Buckley et al. | 206/523 |
| 4,573,569 | 3/1986 | Parker | 206/483 |

FOREIGN PATENT DOCUMENTS 961577  4/1957  Fed. Rep. of Germany ...... 206/446

Primary Examiner—Stephen P. Garbe
Assistant Examiner—Brenda J. Ehrhardt
Attorney, Agent, or Firm—Basile, Weintraub & Hanlon

[57] ABSTRACT

A carrying case for carrying a plurality of disposable insulin syringes is constructed in a fashion such that syringes may be carried in the case either in a plunger-extended, filled condition or with the syringe empty and the plunger fully seated in the syringe.

2 Claims, 3 Drawing Figures

CARRYING CASE FOR INSULIN SYRINGES

BACKGROUND OF THE INVENTION

Nearly all diabetics on insulin find it necessary to have constant access to a supply of insulin which may be injected to maintain their sugar balance. In the typical case, the patient will follow a set routine under which an injection is taken at a certain time and place each day. However, departures from this normal routine, combined with the ever present possibility of a sudden abnormal change in sugar balance, make it desirable for the diabetic person to have insulin and a syringe readily available at all times.

Disposable or one-use type syringes for this purpose are readily available and various kits or devices for carrying such syringes and a supply of insulin and other paraphernalia are known in the prior art. However, many of these prior art kits fail to take into account the fact that the syringe may have to be used on an emergency basis under conditions such that the user may encounter difficulties in filling the standard disposable syringe with insulin in preparation for the injection. The standard disposable syringe employs a plunger which is drawn back from one end of the syringe barrel to fill the syringe through the needle which is held within a supply of insulin during the filling operation. A reasonable amount of dexterity is required to hold the barrel and needle in operative relationship with a relatively small vial with one hand while extending the plunger with the other to transfer the insulin from the vial to the syringe. Prior art kits of which I am aware make provision for carrying the syringe only when the plunger is fully inserted into the syringe barrel. The plunger cannot be so positioned unless the barrel is empty. Many diabetics would have a greater sense of security if the disposable syringe could be stored when filled with insulin.

The present invention is directed to a carrying case in which a plurality of disposable syringes may be safely stored and carried with any selected number of the syringes filled with insulin.

SUMMARY OF THE INVENTION

A carrying case embodying the present invention takes the form of a generally rectangular box having a hinged top cover, the overall dimensions of the box being generally comparable to those of a video tape cassette. A first pad of sponge-like resilient material is bonded or otherwise secured to the interior of the box to extend transversely from one longitudinal sidewall to the other and from one end wall longitudinally of the box roughly two-thirds of the length of the box to terminate a free edge parallel to the end wall. A second pad is bonded to the interior of the box to similarly extend transversely from one longitudinal sidewall to the other and from the other end wall longitudinally of the box to terminate at a free transverse edge parallel to and spaced approximately one inch from the free edge of the first pad. The thickness of the pads is only slightly less than the depth of the interior of the box.

Longitudinal slots extend through both pads from the free edges of the pads with the slots in the respective pads longitudinally aligned to each other and parallel to the longitudinal sidewalls of the box. The length of the slots in the first pad is such that the barrel portion of a disposable syringe of standard construction may be received and resiliently held within the slot in the first pad with the transversely projecting finger grip flanges of the syringe lying against the free edge of the first pad. The finger grips and plunger cover of the empty syringe may be disposed in the space between the free edges of the first and second pads. If the syringe is filled, its projecting plunger is resiliently received and retained in the opposed slot in the second pad.

Other objects and features of the invention will become apparent by reference to the following specification and to the drawings.

IN THE DRAWINGS

Figure 3:
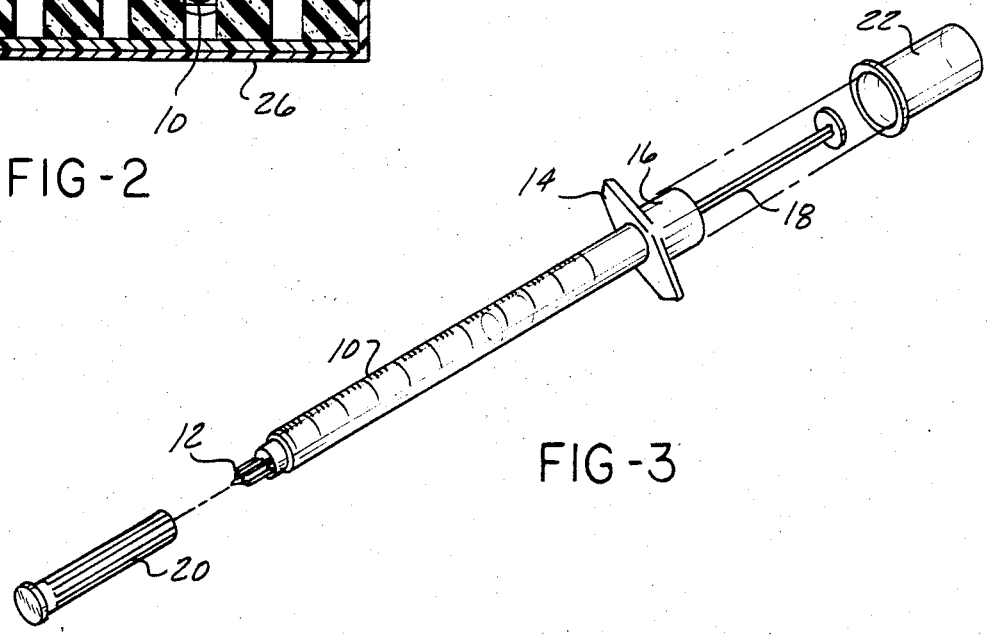
FIG. 3 is a perspective view of the components of a disposable syringe of standard construction which the case of FIG. 1 is designed to store.

The carrying case of the present invention is specifically designed to store a plurality, typically seven, disposable insulin syringes of a standard, commercially available construction, a disposable syringe of the type under consideration being shown in FIG. 3.

Referring first to FIG. 3, the disposable syringe includes an elongate, hollow tubular barrel 10 having an internal chamber communicating with a hollow needle 12 located at one end of the barrel. At its opposite end, the barrel is formed with an integral, transversely extending flange 14 constituting a finger grip, and a somewhat enlarged diameter section 16 projects integrally from the flange. A syringe plunger 18, shown in its fully extended position in FIG. 3, slidably passes through the end section 16 and carries, within barrel 10, a piston slidably engaged with the walls of the internal chamber to expel insulin contained in chamber 10 when the plunger is advanced from the extended position shown in FIG. 3 into the barrel in a well-known manner. A needle shield 20 is normally detachably mounted upon the left-hand end of barrel 10 as viewed in FIG. 3 to enclose and shield the needle, while a closure cap 22 may be frictionally fitted onto projection 16 when plunger 18 is fully inserted into barrel 10 to enclose the opposite end of the barrel. These syringes are available from many commercial sources and are intended to be discarded after a single use. For a syringe having a maximum capacity of 100 units of insulin, the overall length of the syringe with needle shield 20 and closure cap 22 in place (see lowermost syringe in FIG. 1) is approximately 12 cm, while the overall length of the syringe with needle shield 20 in place and plunger 18 fully extended (see upper syringe in FIG. 1) is approximately 17.5 cm.

Figure 1:
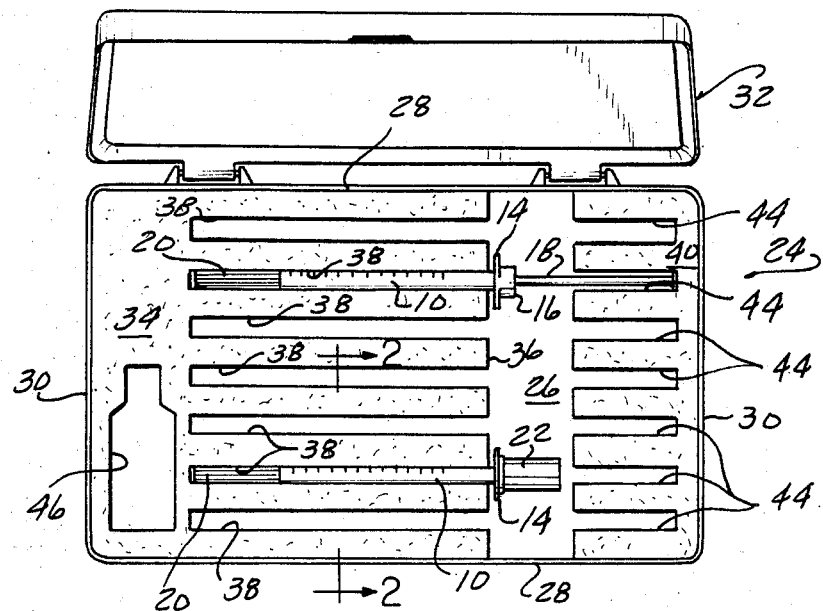
FIG. 1 is a top plan view of a carrying case embodying the present invention.
Figure 2:
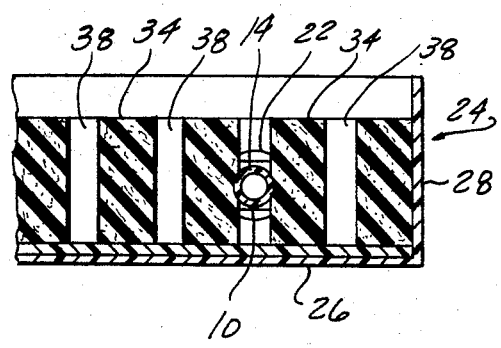
FIG. 2 is a detail cross-sectional view of the case of FIG. 1 taken on the line 2—2 of FIG. 1.

Details of the carrying case designated generally 24 embodying the present invention are shown in FIGS. 1 and 2. The case includes a rectangular box having a bottom 26 of rectangular shape integrally formed with continuous, upwardly projecting longitudinal sidewalls 28 and end walls 30 which may be economically produced in an injection molding process from any of several thermoplastic materials. A hinged cover 32 of similar material, shown in an open position in FIG. 1, constitutes a closure to the case.

A first pad 34 of a resilient, sponge-like material is adhesively bonded or otherwise secured in the interior of box 10 to extend transversely of the box from one longitudinal sidewall 28 to the other and to extend longitudinally within the box from one end wall 30 to a transversely extending free edge 36 parallel to end wall 30. As best seen in FIG. 1, the first pad 34 extends approximately two-thirds of the length of the box and, as best seen in FIG. 2, the thickness of pad 34 is slightly greater than the maximum transverse dimension of the finger grip flange 14 of the syringe. A plurality of parallel, longitudinally extending slots 38 extend through the entire thickness of pad 34 and longitudinally from free edge 36 of pad 34 by a distance which slightly exceeds the length of the syringe barrel 10 with a needle shield in place. The transverse width of slots 38 is such, as best seen in FIG. 2, as to resiliently grip and hold the barrel 10 of a syringe.

A second pad 40 of a resilient, sponge-like material is similarly bonded in the interior of the box at the end of the box opposite first pad 34. Like the pad 34, the pad 40 extends transversely entirely between sidewalls 28 and extends from its end wall 30 to a free edge 42 parallel to and spaced from the free edge 36 of pad 34. Pad 40 is the same thickness as pad 34 and is similarly formed with longitudinal through slots 44 which extend from free edge 42 a distance sufficient to resiliently receive and hold the extended plunger 18 of a syringe whose barrel 10 is received within an aligned slot 38 in pad 34.

It is believed apparent from the foregoing description that the case 24 is capable of safely holding a plurality of disposable syringes either in a sealed, empty condition as is the case with the lowermost syringe shown in FIG. 1 or with the syringe partially or fully filled and its plunger partially or fully extended as is the case with the uppermost syringe shown in FIG. 1.

The case itself may be produced quite inexpensively from synthetic materials. The pad 34 may be provided with a pocket 46 conformed to receive a vial of insulin. In the drawings, the case is shown as having a capacity of seven disposable syringes, which represents a normal weekly supply for the typical diabetic.

While one embodiment of the invention has been described in detail, it will be apparent to those skilled in the art the disclosed embodiment may be modified. Therefore, the foregoing description is to be considered exemplary rather than limiting, and the true scope of the invention is that defined in the following claims.

I claim:

1. A carrying case for storing a plurality of disposable insulin syringes having an elongate syringe barrel, a needle at one end of said barrel, a removable needle shield detachably mounted on said one end of said barrel, a plunger slidably received in said barrel and projecting from the other end of said barrel, and a closure cap detachably mounted on said other end of said barrel to enclose said plunger when said plunger is at its maximum projection into said barrel, said case comprising a box having a rectangular bottom and continuous side and end walls projecting upwardly from said bottom, said sidewalls having a length exceeding the length of a syringe with a needle shield mounted thereon and the plunger at its maximum extension from said barrel, a first pad of resilient material fixedly mounted within said box extending transversely of said box from one sidewall to the other and extending longitudinally of said box from one end wall to a free edge parallel to the other end wall and spaced from said other end wall by a distance greater than the length of a syringe barrel with a needle shield mounted thereon, means defining a plurality of like spaced parallel slots through said first pad extending from said free edge toward said one end wall parallel to said sidewalls, said slots having a length at least equal to the length of a syringe barrel with a needle shield mounted thereon and a width less than the diameter of a syringe barrel such that a syringe barrel placed within said slot will be resiliently gripped by and held between the opposed walls of said slot, a second pad of like material fixedly mounted within said box extending transversely of said box from one sidewall to the other and extending longitudinally of said box from the other end wall to a free edge parallel to and spaced from the free edge of said first pad by a distance greater than the length of a closure cap of a syringe, means defining a plurality of like spaced parallel slots through said second pad extending from the free edge of said second pad toward said other end wall in respective longitudinal alignment with the slots in said first pad, said slots in said second pad having a length and width such that an extended plunger of a syringe placed therein will be resiliently gripped and held between the opposed walls thereof, wherein any selected number of the plurality of syringes may be carried in an extended, filled condition and the remainder of the plurality of syringes in an enclosed, empty condition.

2. The invention defined in claim 1 further comprising means defining a pocket in one of said pads conformed to receive and resiliently retain a vial of insulin.

* * * * *